United States Patent [19]

Di Stefano et al.

[11] Patent Number: 4,496,900
[45] Date of Patent: Jan. 29, 1985

[54] NONLINEARITY DETECTION USING FAULT-GENERATED SECOND HARMONIC

[75] Inventors: Thomas H. Di Stefano, Bronxville; Arnold Halperin, Peekskill, both of N.Y.

[73] Assignee: International Business Machines Corporation, Armonk, N.Y.

[21] Appl. No.: 373,318

[22] Filed: Apr. 30, 1982

[51] Int. Cl.³ ............................................. G01N 27/00
[52] U.S. Cl. ..................................... 324/51; 324/71.1; 29/574
[58] Field of Search ............ 29/574; 324/51, 52, 324/64, 71 R

[56] References Cited

U.S. PATENT DOCUMENTS

| | | | |
|---|---|---|---|
| 2,758,276 | 8/1956 | Foerster | 324/34 |
| 3,299,351 | 1/1967 | Williams | 324/52 |
| 3,500,188 | 3/1970 | Whitley | 324/64 |
| 3,624,496 | 11/1971 | Feinstein | 324/64 |
| 3,733,545 | 5/1973 | Elsner | 324/52 |

OTHER PUBLICATIONS

H. E. Meier, "Circuit Board Testing," IBM Technical Disclosure Bulletin, vol. 23, No. 9, Feb. 1981, p. 4092.

Primary Examiner—Stanley T. Krawczewicz
Assistant Examiner—Jose M. Solis
Attorney, Agent, or Firm—Carl C. Kling

[57] ABSTRACT

The tester and method for nondestructively detecting nonlinearity faults in conductors includes the application of a composite AC and DC drive signal to the device under test in such manner that nonlinearities in the device under test produce fault signals including second harmonics, due to local changes of resistance caused by ohmic heating. Electronic filters are used to select out and amplify the second harmonic only, eliminating the direct current and fundamental frequency components of the initial test pulse, plus third and subsequent harmonics. The filtered second harmonic signals from the device under test are then phase-compared to a phase-shifted second harmonic signal produced by a frequency doubler from the test signal generator oscillator to cancel out the second harmonic signals from the good conductor; the remaining phase anomaly signals control a threshold detector remaining to provide fault indication.

5 Claims, 14 Drawing Figures

POSITIVE SECOND HARMONIC

NEGATIVE SECOND HARMONIC

NONLINEARITY DETECTION USING FAULT-GENERATED SECOND HARMONIC

BACKGROUND OF THE INVENTION

1. Field of the Invention

This invention relates to techniques for nondestructive testing of conductors for constrictions and discontinuities that escape standard conductivity testing.

2. Description of the Prior Art

A significant and increasingly difficult problem with packaging and interconnection systems in complex circuits, such as circuits in computers with high levels of integration, is the detection of incipient opens that escape standard conductivity testing of conductors.

A number of third harmonic techniques have been used to study electrical conductors. Typical of such third harmonic testing methods is that described in U.S. Pat. No. 3,733,545, Elsner et al., Method for Locating Nonlinear Mechanical Junctions of Metallic Electrical Conductors, May 15, 1973. Another third harmonic measuring technique is described in U.S. Pat. No. 3,500,188, Whitley et al., Method and Means for Measuring Constriction Resistance Based on Nonlinearity, Mar. 10, 1970.

Fault location techniques involving the second harmonic have also been used. For example, U.S. Pat. No. 3,299,351, D. L. Williams, Apparatus for Detecting Faults in Buried Cables Including Means for Applying a Composite Signal Having Fundamental and Even Harmonic Frequency Components, Jan. 17, 1967, describes a technique for providing a composite signal of a fundamental frequency and even harmonics. Williams deliberately impresses the second harmonic as the test current—measures the polarity of the potential due to the composite signal flowing into the ground at the fault location—to find the location.

Prior art testers have been minimally successful in locating current constricting defects and other nonlinearities which accompany incipient faults, because the electrical effects of linear resistances normally present along the conductor swamp the electrical effects of the nonlinearity being tested for. Attempts to overcome these "good line" signals can result in destruction of good lines, aggravation of incipient faults without detection of the fault, or false detection of faults in good circuits.

Testers in the prior art have not operated by impressing a DC biased fundamental frequency AC signal on the conductor to be tested (so as to cause both linear characteristic "good line" signals including second harmonics and nonlinearity signals including second harmonics), balancing out the second harmonic signals from linear impedance characteristics of the "good line" conductor, and detecting the second harmonic signals caused by the fault.

SUMMARY OF THE INVENTION

The invention is a non-destructive apparatus and method for detecting current constricting defects (such as cracks, narrow conductors, line breaks, intermittent opens, etc.) in conductors by examining the second harmonic voltages produced by passing a composite AC plus DC signal through the conductor, the test signal generator is balanced and adjusted to provide a signal which is symmetrical and thus provides little even harmonic distortion. The second harmonic voltages across the conductor result primarily from conductor nonlinearities (incipient faults) and the use of the second harmonic technique provides testing capability for such nonlinearities which are not detectable by ordinary testing techniques. The theory of operation depends upon local changes of resistance caused by ohmic heating in nonlinearities which, while conductive, might be expected to fail early during the normal life of the conductor. The composite alternating current plus direct current test signal passes through the conductive path being tested in an unbalanced wave and, upon encountering a local constriction, causes a small volume of metal in the constriction rapidly to heat and cool in a fashion to generate second harmonic signals in close phase relationship to the unbalanced wave. This temperature change produces a resistance change which varies monotonically with the temperaure in response to the AC plus DC current at the frequency of the resistance change. The resistance change produces time varying voltage components at frequencies including the fundamental frequency, second harmonic, third harmonic, fourth harmonic and additional harmonics.

The second harmonic signal is the largest signal easily distinguished from the fundamental; it is the second harmonic signal that is amplified and detected.

This nonlinearity-generated signal may be several orders of magnitude smaller than very similar signals reflected from a good conductor of relatively great length, occurring as a result of resistance heating. There is, however, a phase difference which permits the good conductor generated signals to be filtered out, thus isolating the constriction defect generated signal.

A feature of the invention is the use of the second harmonic nonlinearity-generated signal ($2f_0GV$) together with phase detection to eliminate the effects of good conductor signal reflections ($2f_0CV$).

Some of the advantages of using second harmonic signals are:

(1) Symmetrically balanced signal sources have more inherent third harmonic distortion than second. Thus, the ultimate sensitivity of the second harmonic signal is greater.

(2) Amplifiers that are used to detect the signal will distort more at $3f_0$ than $2f_0$. This gives erroneous signals.

(3) The DC drive signal can be used in testing for $2f_0GV$ and is proportional to the signal generated. In third harmonic testers, the DC has no effect.

The object of the invention is to detect incipient or intermittent faults in circuit patterns, which faults are not detectable through ordinary testing techniques.

DESCRIPTION OF THE PREFERRED EMBODIMENT

Figure 1:
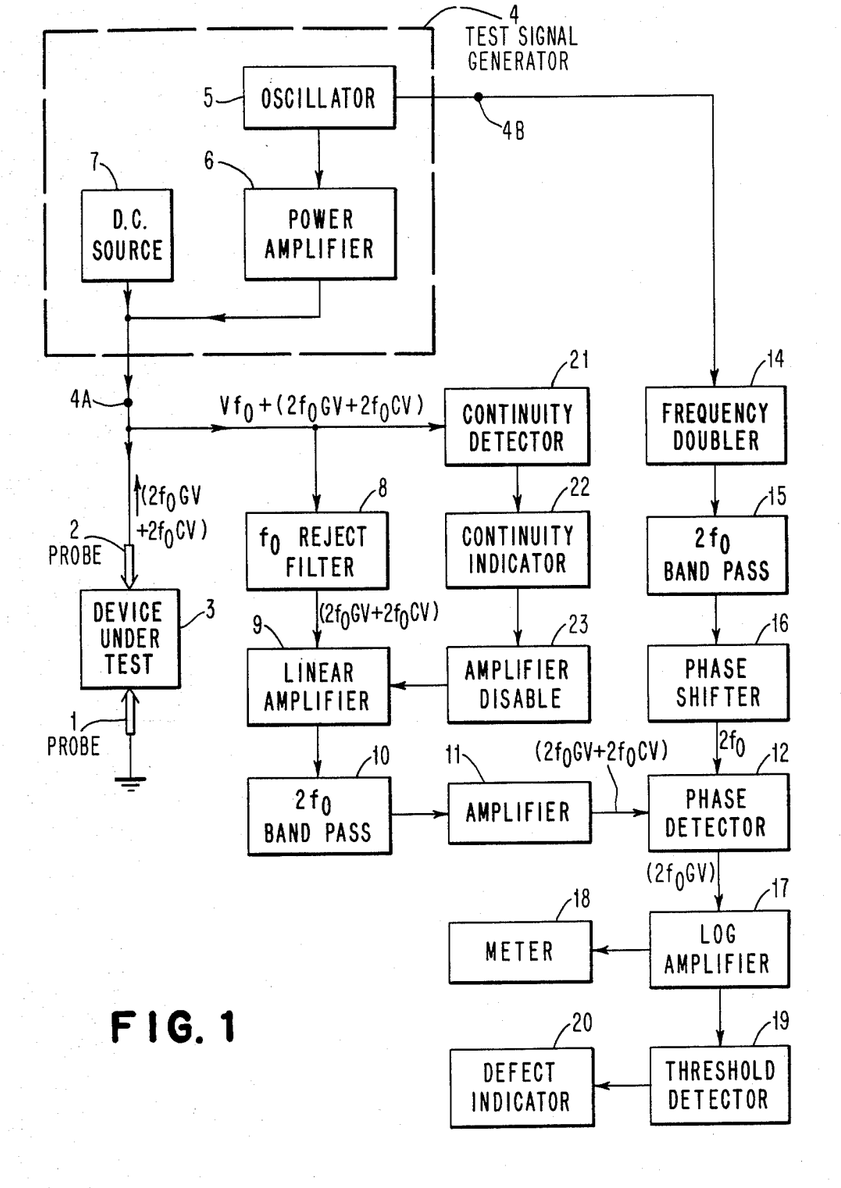
FIG. 1 is an electrical block diagram showing the invention in operation.

FIG. 1 is a block diagram of the tester of the invention. Probes 1 and 2 connect the circuit on the device 3 under test (which may be a printed circuit board) to a composite test signal tap 4A on test signal generator 4, which comprises oscillator 5 and power amplifier 6, and DC source 7. The test signal from tap 4A is applied via probes 1 and 2 to the appropriate circuit of device 3 which is under test. If the device under test is free of nonlinearity of faults there will be no significant fault-generated harmonics. If, however, the device under test contains a nonlinearity (such as a crack which is subject to ohmic heating) there will be a nonlinearity fault-generated signal including harmonics. The second harmonic is most significant.

The device under test is connected to $f_0$ reject filter 8 to reject the test signal fundamental frequency ($f_0$) and, of course, the test signal direct current component. The output of filter 8 is amplified by linear amplifier 9, filtered through a second-harmonic band pass filter 10 and amplifier 11, and provided to phase detector 12. Phase detector 12 thus has applied to it, from amplifier 11, the amplified second harmonic generated by the nonlinearity fault of the device under test. In order to determine the scope of the nonlinearity fault, phase detector 12 has applied to it a second harmonic signal, from $f_0$ tap 4B, derived from oscillator 5 of the test signal generator 4. The fundamental frequency is doubled by frequency doubler 14, filtered through band pass filter 15 at $2f_0$, and phase shifted by phase shifter 16. In order to reduce the noise on the relatively small second harmonic signal generated by the nonlinearity fault, and to obtain phase discrimination from signals generated along the length of a good conductor, the fault signal is phase-sensitive-demodulated and converted to a direct current voltage. This direct current voltage is amplified by logarithmic amplifier 17 to get a wide range of readings. The output of amplifier 17 can be connected to a meter 18 or a go, no-go threshold detector 19 with a defect indicator 20 such as an indicator light, marker or sorting device.

In order to make the tester easy to use, a continuity detector 21 and continuity indicator 22 are used. When continuity is not made between the probes and the device under test, the linear signal amplifier is disabled by amplifier disabling circuit 23 so false readings are not made.

THEORY AND OPERATION

The theory of operation depends upon second harmonic signals generated from a local change of resistance caused by ohmic heating at the nonlinearity and the characteristic heating-cooling cycle at the nonlinearity which differs markedly (as to phase) from the characteristic heating-cooling cycle of the conductor along its length. Cooling at the nonlinearity is fast, due to conductive heat transfer to adjacent volumes of cooler metallic conductor, and heating is relatively fast because of conductor constriction, localized higher currents, eddy currents and localized heat buildup causing even higher resistances. The heat cycle is closely related to the phase of the AC signal.

Cooling along the length of the good conductive element is relatively slow, and heat buildup to a maximum occurs due to the heat insulating properties of the insulation and the fact that incremental volumes of the metallic conductor have no adjacent volumes of cooler metallic conductor. The heat cycle is not closely related to the phase of the AC signal, differing by approximately 90°. When a current source consisting of an alternating current with a direct current flows through a constricted conductor, the small volume of metal rapidly heats and cools asymmetrically on the half wave enhanced by the DC bias. This produces a resistance change which varies monotonically with the temperature change. The current flowing through this changing resistance produces a voltage response which has nonlinear components including even harmonics of the current drive.

When a small defect exists in a long conducting line, it is normally difficult to distinguish between second harmonic signals from the defect and second harmonic signals from the line. In fact, the second harmonic generated signal from a good conducting line could be much greater in amplitude than the signal from a defect.

In order to distinguish between the two signals, some characteristic differences should be recognized. In a defect, the temperature rise and fall due to the drive signal follows the power waveform closely, because of a short thermal time constant, producing resistance changes and second harmonic voltage changes of a particular phase. In a long conducting line, the temperature rises and falls due to the drive signal are integrated, due to long thermal time constants, and the resulting second harmonic generated voltage is phase-shifted with respect to the signal from a defect.

If the phase detector is aligned so that the second harmonic from a long conducting line is nulled out, only defect signals will be detected.

It should be noted that an optimum drive frequency should be used so that the amplitude of the signal from a good conductor is small and yet should have a large phase difference from the signal due to a defect.

Because the heating and cooling in a long conducting line is integrated, higher frequencies cause a smaller signal. At some higher frequency, the signal from the defect will become smaller and will phase shift. Therefore, the optimum frequency of operation is one that is high enough to provide a small signal from the conducting line and low enough so that the defect signal is not reduced or phase-shifted.

The drive current is $I = I_0 + I_1 \sin \omega t$; the resistance change with temperature is $r = r_0 (1\alpha\Delta\tau + \beta(\Delta\tau)^2 + \gamma(\Delta\tau)^3 \ldots )$. $\alpha$ is a constant. For copper it is 0.00393 per °C. $\Delta\tau$ is equal to K times the power dissipated at the construction. K depends on the physical dimensions of the constriction and other components producing the thermal time constant. Dimensions of K are °C./watt.

The sine wave source is balanced in such a way as to minimize the second harmonic signal when no defect is present in the conductor under test. It is essential to the operation of this second harmonic technique that the source current contain both a DC and a pure sine wave AC component. Without the DC component, a non-linearly conductive defect would produce a voltage signal containing only odd harmonics.

In implementing this technique for detecting nonlinear conducting elements, the third harmonic component is not detected, as is done in the prior art, because the third harmonic produced by the defect would be mixed with the signal resulting from third harmonic impurity in the source current. The source impurity would then mask the presence of any nonlinear conductivity due to a conductor defect. Typically, a sine wave current source will exhibit large odd harmonic impurities (including the third) that are due to crossover distortion, saturation, etc., that cannot be eliminated by carefully balancing the circuitry. By detecting the second harmonic signal produced by a pure DC plus a carefully balanced AC source, instead of detecting the third harmonic, a sensitivity to nonlinearities several orders of magnitude larger than previous methods is obtained.

Figure 2A:
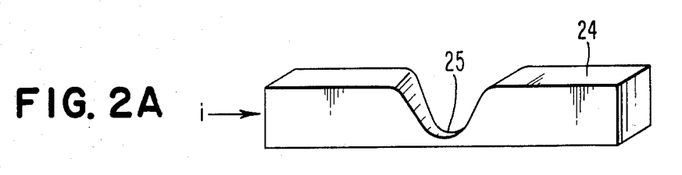
FIG. 2A is a diagrammatic presentation of a resistive constriction in a conductor.
Figure 2B:
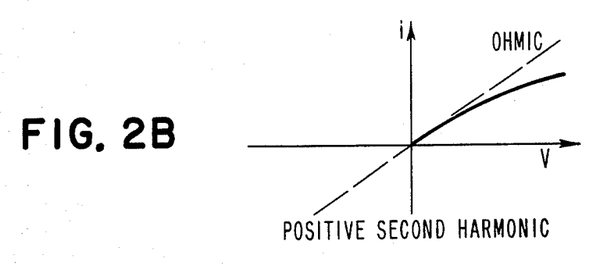
FIG. 2B is the related current/voltage chart.
Figure 7:
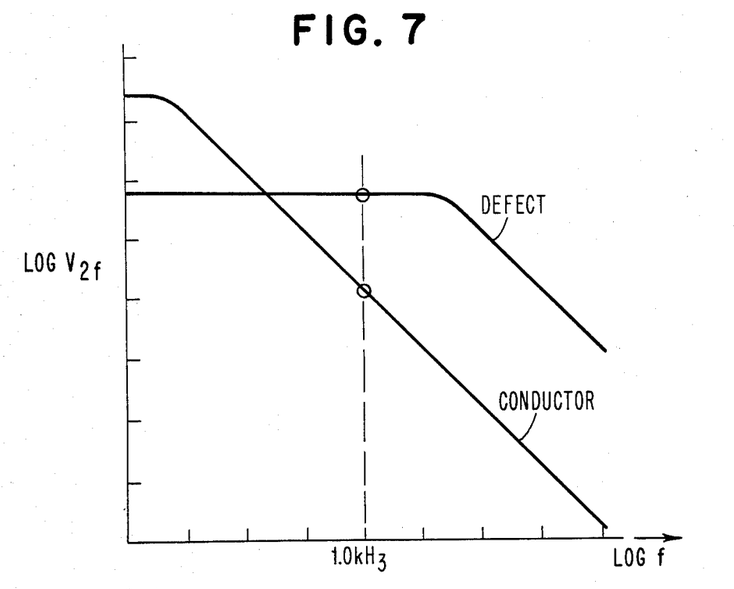
FIGS. 7–12 are graphs showing the voltage/frequency/phase/resistance relationships of signals produced during testing by the normal resistance heating of the conductor and by the dynamics of the defect.

The theory of operation is described for a model current constriction as shown in FIGS. 2 and 2B. The approximation is made that the constriction cools by conduction of heat out to the main body of the conductor. The second harmonic voltage produced by a current $i = I_0 + I_1 \cos 2\pi ft$ is:

$$V_{2f} = I_0 I_1^2 \frac{\alpha \rho^2}{24\sigma} \left(\frac{d}{a}\right)^3 \left\{ \frac{2}{1 + j\frac{\pi fCd^2}{4\sigma}} + \frac{1}{1 + j\frac{\pi fCd^2}{2\sigma}} \right\}$$

$$V_{2f} \cong I_0 I_1^2 \left(\frac{3\alpha}{24\sigma\rho}\right) R^3$$

where $\alpha$ is the temperature coefficient of resistance of the conductor, $\rho$ is the conductor resistivity, $\Sigma$ is the thermal conductivity, C is the heat capacity of the metal, a is the area of a cross section of the construction in mils$^2$, d is the defect length in mils. and R is the total resistance of the constriction. The second harmonic signal falls with frequency above the cut-off frequency $f_c = (8c/\pi d^2)$, as illustrated by the curve labeled "Defect" in FIG. 7.

As shown in FIG. 2A, conductor 24 has a resistive constriction 25. Local heating at constriction 25 produces a positive second harmonic current/voltage response different from that of a linear ohmic device as shown in FIG. 2B.

Figure 3A:
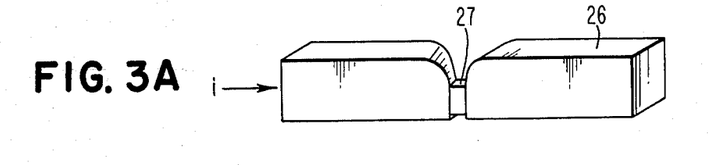
FIG. 3A is a diagrammatic presentation of a tunneling constriction in a conductor.
Figure 3B:
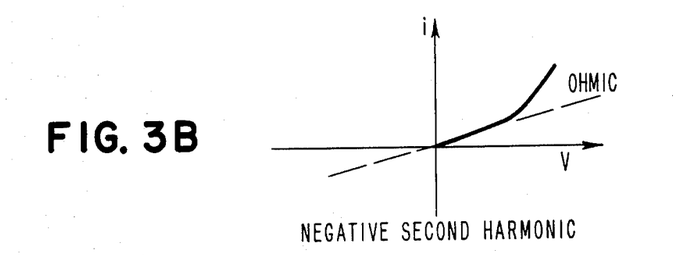
FIG. 3B is the related current/voltage chart.

A conductor 26 may have a tunneling constriction 27, as shown in FIG. 3A. This tunneling constriction produces a negative second harmonic current/voltage response as shown in FIG. 3B. As shown in FIGS. 4-12, the voltage produced across the constriction is composed of a DC component, a fundamental component, the second harmonic component which we are particularly interested in, and higher frequency components.

Figure 4:
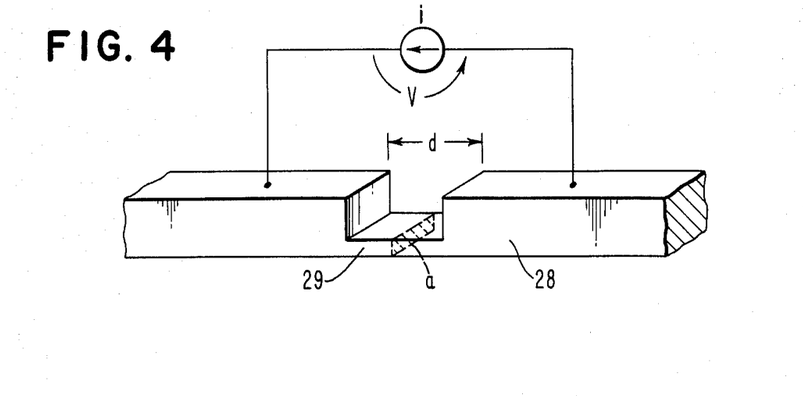
FIG. 4 is a diagrammatic presentation of a nonlinearity in a conductor.

FIG. 4 shows in stylized fashion a conductor 28 having a constriction 29 which may be a resistive constriction as shown or may be a tunneling constriction.

Figure 5:
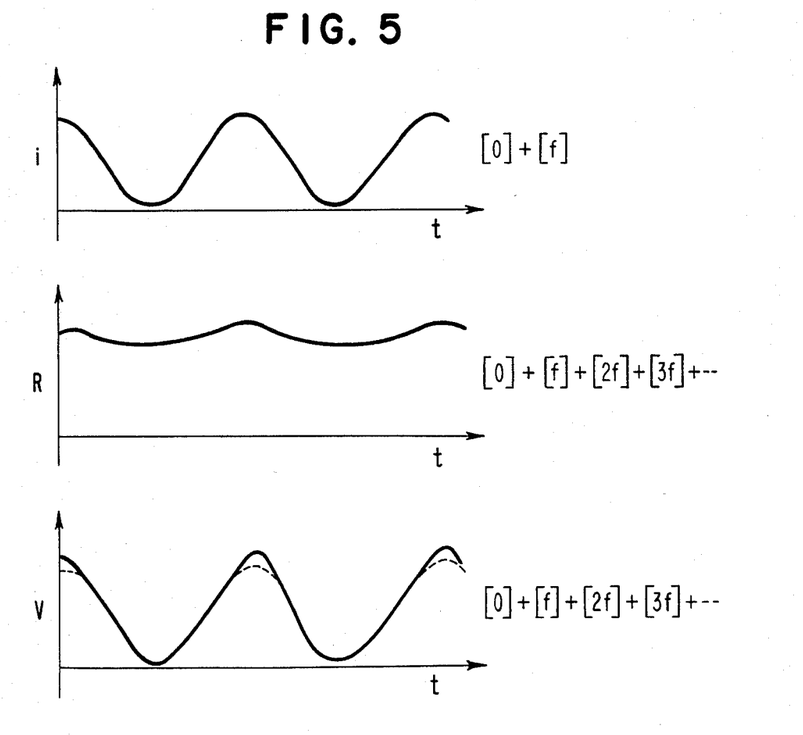
FIGS. 5 and 6 are composite current-resistance-voltage charts on a time scale, showing frequency related effects.

FIG. 5 shows current i, resistance R and voltage V on a time scale with all harmonics included in the R and V waveforms.

Figure 6:
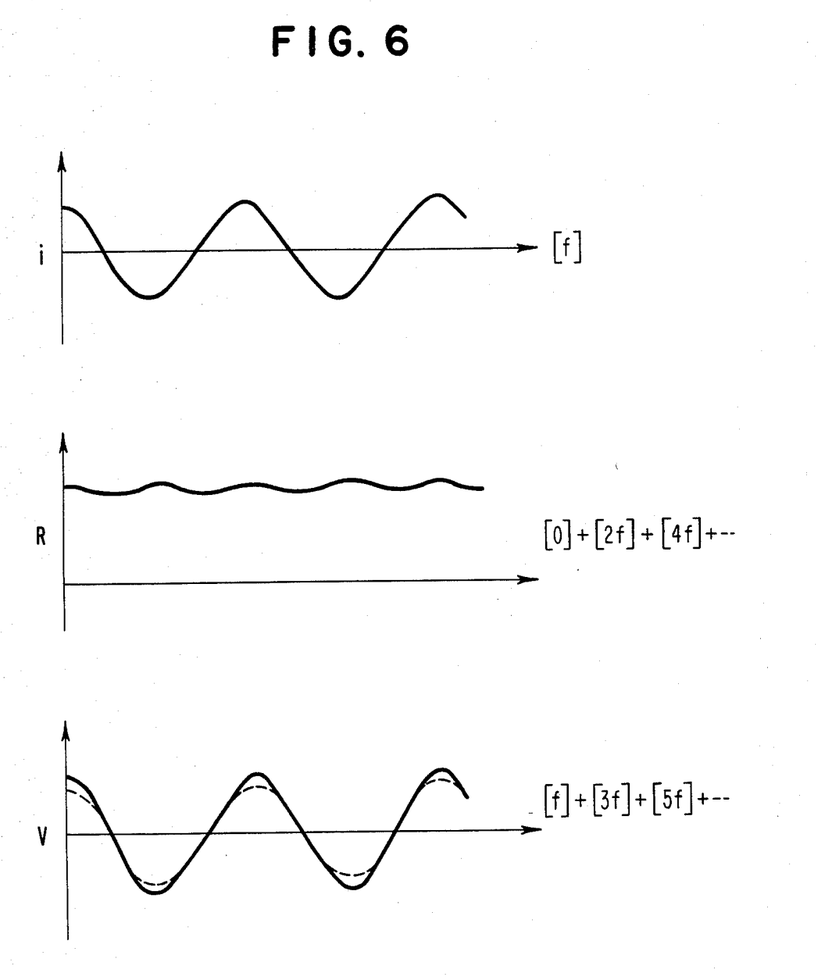

FIG. 6 shows the waveforms for i, R and V for the case in which the drive current i is a pure sine wave with no DC component. The odd harmonics are removed from the R waveform and the even harmonics removed from the V waveform.

FIG. 7 is a graph of log $V_{2f}$ over log f, showing a respesentative reference line at 1.0 KHz. The voltage of the conductor diminishes on a different response curve than does the voltage across the defect. With a particular frequency (1.0 KHz shown) the second harmonic voltage generated by the defect is near a maximum difference from the second harmonic voltage generated by the conductor.

Figure 8:
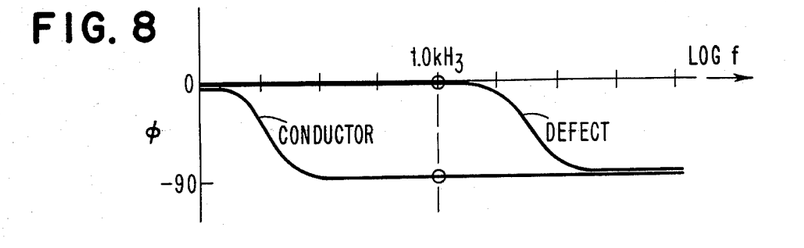

FIG. 8 is a diagram illustrating the phase difference of the second harmonic signals related respectively to the conductor and to the defect. The defect second harmonic signal closely follows the phase of the applied test signal up to a finite saturation frequency (here shown as >1.0 KHz) while the conductor second harmonic signal lags 90° at the same frequency.

Figure 9:
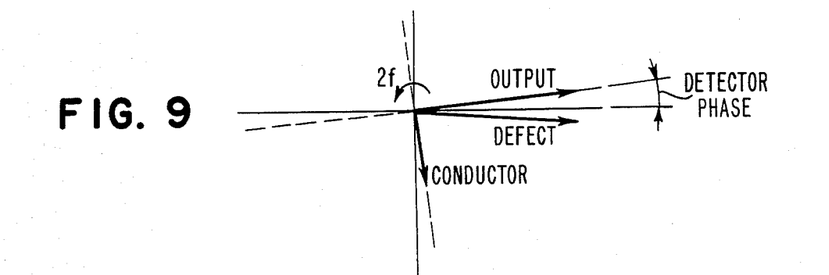

FIG. 9 illustrates the phase detection to discriminate defect signals from conductor signals.

Oscillator 5 (FIG. 1) produces a low distortion sine-wave signal which is buffered by amplifier 6 which provides a high current drive. This is applied through the device 3 under test. A direct current is also applied to the device 3 under test. If a constriction causing heating is encountered, a second harmonic is generated. This second harmonic generated voltage ($2f_0GV$) appears with the driving signal and is very small compared to the drive signal. The fundamental signal $V_{f0}$ is rejected by a filter 8 and the remaining signal is amplified, filtered again, and amplified. The remaining signal has a large component ($2f_0CV$) due to resistance heating along the length of the conductor. In order to null the effect of the $2f_0CV$ noise, the signal is phase-sensitive-demodulated by phase detector 12 and converted to a direct current voltage. This DC voltage is filtered as required by filtering means in phase detector 12. Log amplifier 17 converts to the signal so it can be recognized over 4 to 5 decades of $2f_0GV$ strength. In order to operate the phase-sensitive-detector, a synchronous signal from the oscillator is derived from frequency doubler 14, $2f_0$ band pass filter 15 and phase shifter 16. In order to make the tester easy to use, a continuity detector 21 and continuity indicator 22 are used. Threshold detector 19 and defect indicator 20 are also for ease of use. Both these indicators are placed so that an operator can easily find defects. When continuity is not made between the probes to the device under test, the linear signal amplifier is disabled so false readings are not made.

Devices under test showing $2f_0GV$ have been found to fail in accelerated life test significantly sooner than those not showing $2f_0GV$.

DEFECT THEORY AND CALIBRATION

FIG. 9, shown on 2f scale, illustrates calibration of phase detector 12 of FIG. 1. For use in testing a sample, the tester may be calibrated for maximum detection of a detector phase to be selected from a range centered slightly above 0° out of phase with the AC component of the test signal so as to maximize discrimination between the 0° phase of the defect second harmonic signals and the near 90° phase of the good conductor signals. See FIG. 8. Calibration may be done by using as a standard a circuit with known defects or as a standard a circuit known to be defect free.

Figure 10:
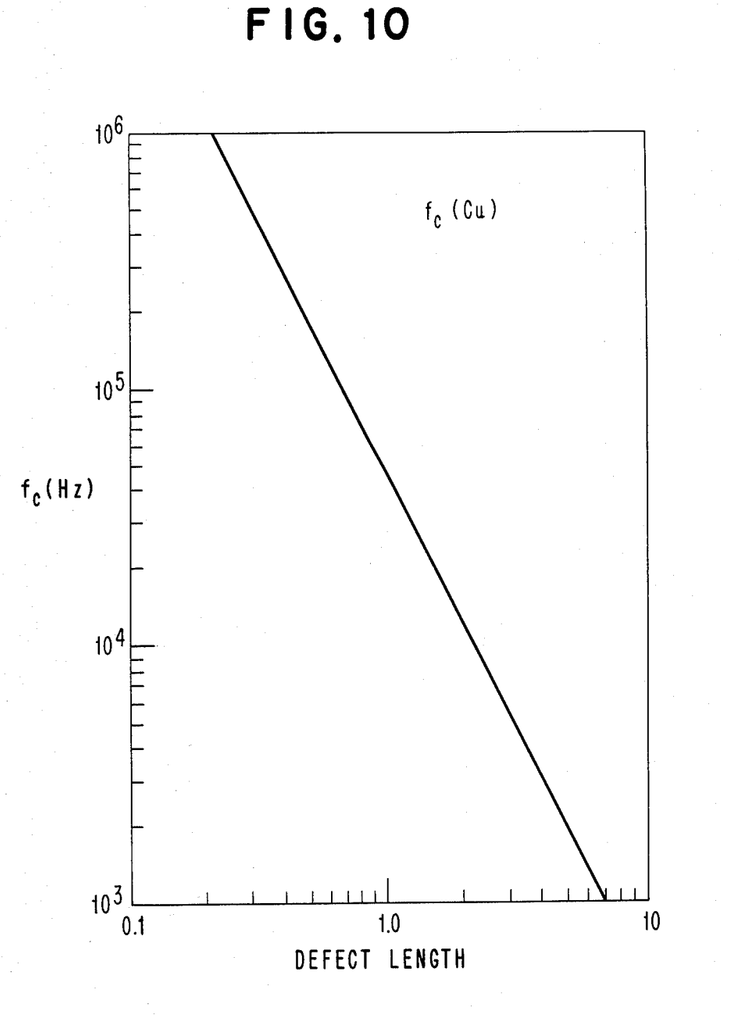

FIG. 10 is a graph illustrating some of the properties of copper. The unit of the abscissa is the mil; the unit of the ordinate is frequency in Hertz. Cutoff frequency tends to increase as a function of decreasing length of the defect. Calibration may be optimized by the operator by selection of a frequency appropriate to the type of defect suspected.

Frequency $f_c$(Hz) is the test frequency; the line shows the frequency at which there is 3 Db rolloff, where the response is down by a factor of two. Defect length is in mils (mil=1 inch=0.0254 mm). For example, at an expected defect length of 1.0 mils (0.0254 mm), the operator would calibrate the tester at 50,000 Hz or below.

Figure 11:
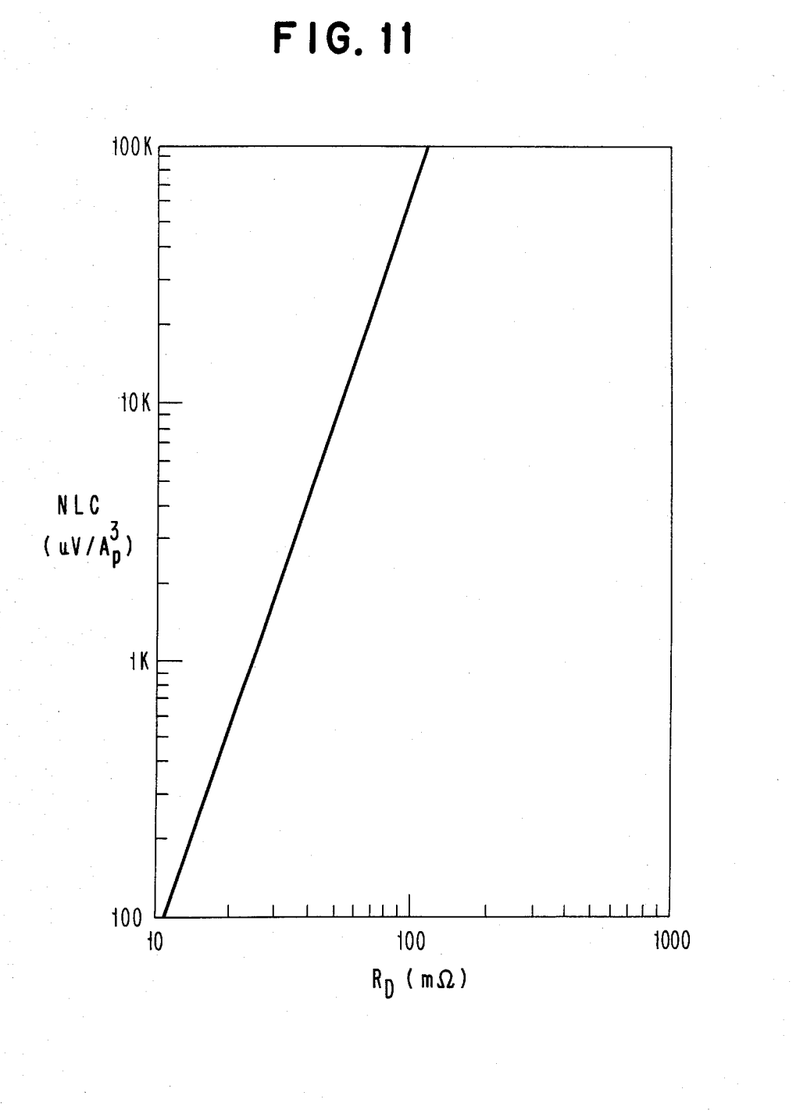

FIG. 11 is a theoretical graph of nonlinear conductivity of copper as a function of defect resistance. The nonlinear conductivity (NLC) tends to increase as the resistivity of the defect ($R_D$) increases.

Figure 12:
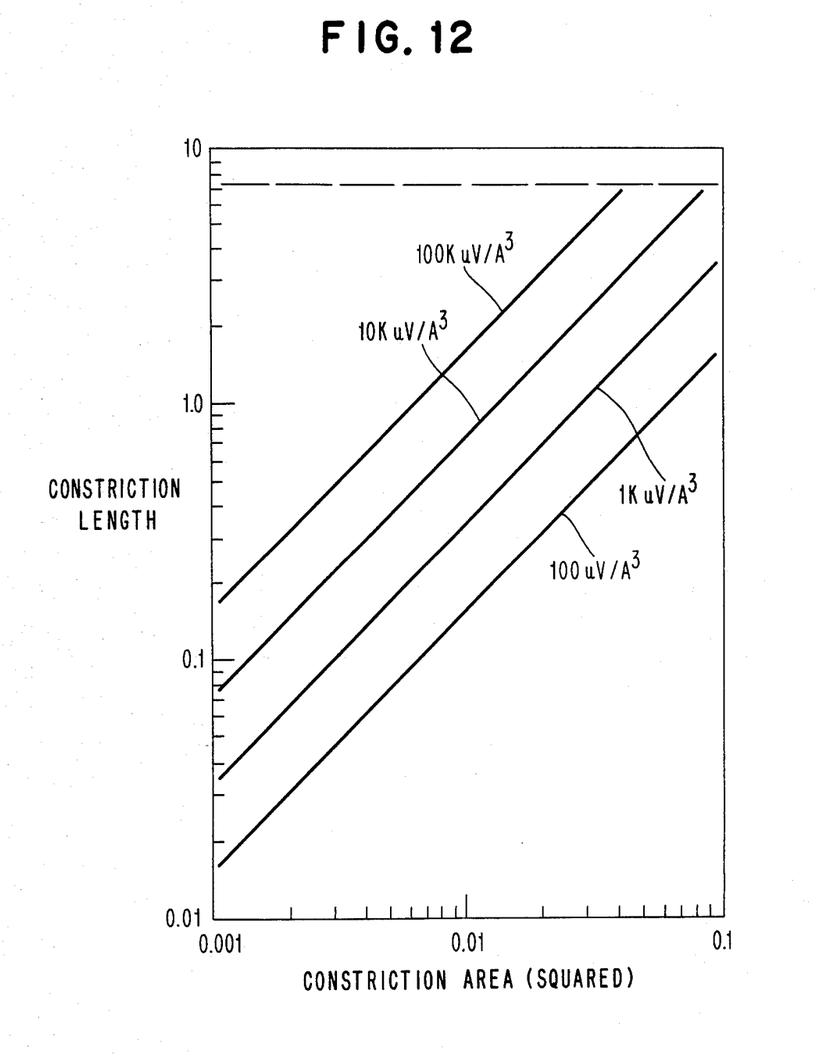

FIG. 12 is a theoretical explanation in graphical form. FIG. 12 relates the length and area of a hypothetical defect in copper with the predicted second harmonic generation. Abscissa numbers are in units of (mil)$^2$. The ordinate numbers are in mils. Note that the numbers are on a log scale—note also that other units are appropriate for other materials. The construction lengths and constriction areas are related to those shown in FIG. 4 as length d and area a. FIG. 12 shows that there are ranges of defects which may be tested for; these defects have differing second harmonic voltage levels. Certain metallurgies may tend to have larger defects, or lower conductivity, than other metallurgies, and thus the tester may require differing calibration. The lines on the graph are in microvolts per Ampere (peak) cubed ($\mu$V/A$^3$). This graph shows that the second harmonic signals from the defect become very small as the defect detection requirement becomes more stringent. Tiny defects produce tiny signals, which continue to be obscured by large signals from the good conductors.

What is claimed is:

1. Test apparatus for determining the existence of nonlinearity faults in a conductor under test, which conductor is connected by probes to the test apparatus, characterized by:
    (a) a test signal generator having a composite test signal node and means to provide at the composite test signal node a composite test signal including a direct current signal of known characteristics and an alternating current signal of known characteristics including a fundamental frequency, and having a fundamental frequency node for providing the fundamental frequency;
    (b) connecting means, for connecting the composite test signal node to a device under test in such fashion that nonlinearity anomalies in the device under test provide fault signals including second harmonics of the fundamental frequency;
    (c) test signal filtering means, connected to said composite test signal node, to pass only the second harmonic signal from the device under test;
    (d) frequency doubling means connected to the fundamental frequency node of said test signal generator to produce second harmonic test signals;
    (e) phase detection means having inputs including an input connection from said filtering means for accepting second harmonic signals from the device under test and having further input means for accepting the second harmonic test signals from said frequency doubling means, for detecting fault signals separate from conductor signals differing in phase; and
    (f) output means for providing an indication of fault in the device under test.

2. Test apparatus according to claim 1, further characterized by:
    (g) a continuity detector connected to said composite test signal node; and
    (h) disabling means connected to said continuity detector and to said test signal filtering means to prevent passage of spurious test signals when continuity is not made.

3. The method of testing an electrical conductor for nonlinearity faults, characterized by:
    (a) probing the device under test with a composite signal including a DC signal and an AC signal at a characteristic test signal fundamental frequency, whereby nonlinearity faults in the conductor under test generate second harmonic nonlinearity signals at a first phase relationship, and whereby resistance characteristics of the conductor under test itself generate relatively large second harmonic conductor signals;
    (b) phase-sensitive-demodulating such fault-generated second harmonic nonlinearity signals using a predetermined standard signal at second harmonic frequency and phase shift to null the second harmonic conductor signals and identify as faulty a device under test having second harmonic nonlinearity signals differing from the standard signal.

4. The method of claim 3, further characterized by:
    (c) disabling the detecting of spurious second harmonic signals during periods except when continuity has been established.

5. The method of claim 3, further characterized in that the characteristic test signal fundamental frequency of said composite test signal is selected within the range of optimum frequencies above the frequency at which second harmonic signals caused by heating and cooling along the conductor length diminish because of integration, and below the frequency at which second harmonic signals caused by heating and cooling of defects of the expected type begin to diminish.

* * * * *